US00PP08915P

United States Patent [19]

Danziger

[11] Patent Number: Plant 8,915

[45] Date of Patent: Sep. 27, 1994

[54] PETUNIA PLANT NAMED CAS 45

[75] Inventor: Gabriel Danziger, Post Beit Dagan, Israel

[73] Assignee: Florfis AG, Binningen, Switzerland

[21] Appl. No.: 162,350

[22] Filed: Dec. 7, 1993

[51] Int. Cl.[5] ..... A01H 5/00

[52] U.S. Cl. ..... Plt./68.1

[58] Field of Search ..... Plt. 68.1

*Primary Examiner*—James R. Feyrer

*Attorney, Agent, or Firm*—Foley & Lardner

[57] ABSTRACT

A new and distinct cultivar of petunia plant named Cas 45, characterized by the combined features of intense purple-violet flower color, large flowers with dark throat and dark veins, vigorous but bushy growth habit, long, semi-erect plant habit, later becoming overhanging, and medium green foliage.

2 Drawing Sheets

The present invention comprises a new and distinct cultivar of petunia, hereinafter referred to by the cultivar name Cas 45.

Cas 45 was originated from a hybridization made by the inventor Gabriel Danziger in a controlled breeding program in Moshav Mishmar Hashiva, Israel in 1992. The female parent was a seedling designated X 68. The male parent of Cas 45 was a seedling designated Y 75. Both parents are proprietary cultivars used in the breeding program.

Cas 45 was discovered and selected as one flowering plant within the progeny of the stated cross by Gabriel Danziger in 1992 in a controlled environment in Moshav Mishmar Hashiva, Israel.

The first act of asexual reproduction of Cas 45 was accomplished when vegetative cuttings were taken from the initial selection in December 1992 in a controlled environment in Moshav Mishmar Hashiva, Israel, by, or under the supervision of, Gabriel Danziger.

Horticultural examination of selected units initiated in December 1992 and continuing thereafter has demonstrated that the combination of characteristics are herein disclosed for Cas 45 are firmly fixed and are retained through successive generations of asexual reproduction.

Cas 45 has not been observed under all possible environmental conditions. The phenotype may vary significantly with variations in environment such as temperature, light intensity and day length, without, however, any variations in genotype.

The following observations, measurements, and comparisons describe plants grown in Hillscheid, Germany, under greenhouse conditions which approximate those generally used in commercial practice.

The following traits have been repeatedly observed and are determined to be basic characteristics of Cas 45, which in combination distinguish this petunia as a new and distinct cultivar:

1. Intense purple-violet flower color.
2. Large flowers with dark throat and dark veins.
3. Vigorous but bushy growth habit, with branches fully extending in all directions from center of plant.
4. Semi-erect initial plant habit, later becoming overhanging.

Of the commercial cultivars known to the present inventor, the most similar in comparison to Cas 45 is Shihi purple. Reference is made to attached Chart A which compares certain characteristics of Cas 45 to those same characteristics of Shihi purple. In general comparison to Shihi purple, Cas 45 has a shorter plant habit and a more bluish tint of flower color. In addition, in Cas 45 black veining on the surface of the flower covers only the throat and the inner part of the flower, but not the margin of the corolla.

The accompanying photographic drawings show typical flower and foliage characteristics of Cas 45, with colors being as true as possible with illustrations of this type. The photograph on Sheet 1 illustrates Cas 45 cultivated in a hanging basket. The photo on Sheet 2 comprises an enlarged showing of single flowers of the new cultivar.

In the following description, color references are made to The Royal Horticultural Society Colour Chart. The color values were determined indoors in August. Flowers were taken from plants cultivated in hanging baskets in an open greenhouse in Hillscheid, Germany. For the description, the upper parts of the plant were observed or measured.

Classification:

*Botanical.*—A hybrid of the genus Petunia.

*Commercial.*—Petunia cv Cas 45.

INFLORESCENCE

Plant:

*Growth habit.*—Vigorous, but comparatively compact, hanging.

*Plant length.*—90 cm, measured from the base of the stems in the middle of the hanging basket to the tips of the hanging branches (28 week old plants).

*Blooming period.*—Medium early; begins 10 weeks after propagation of unrooted cuttings, continually flowering thereafter.

Stem:

*Thickness.*—Young branches, 3 mm; older branches 5 mm.

*Color.*—Light green, between 137 D.

Pubescence.—Present.

Branching.—8 branches per week.

Length of internode.—30–45 mm.

Leaf:

*Arrangement on stem.*—Opposite, arranged decussately on stem.

*Shape.*—Ovate to narrow-ovate.

*Size (average).*—56 mm long, 32 mm wide, based on largest leaves from a young stem of a plant in flower.

*Thickness.*—Medium.

*Color.*—Medium green, 137 B.

*Pubescence.*—Present.

Flower:

*Orientation at opening.*—The bud and peduncle form an acute angle with the stem; the open flower and peduncle are oriented approximately at right angles to the stem.

*Type.*—Single

*Shape.*—Round, large with undulating margin.

*Diameter.*—80–85 mm.

*Color.*—Upper (inner) surface at opening: 79 B. Under (outer) surface at opening: 83 B near margin. Upper (inner) surface at pollen maturity: Between 74 A and 78 A, but slightly more intense than 78 A. Under (outer) surface at pollen maturity: 80 A. Throat (inner surface): Black. Markings: Black net-shaped veining, not only in the throat but also on the inner part of the corolla.

*Peduncle length.*—40–50 mm.

*Peduncle color.*—Green, partly brown with anthocyanin.

*Reproductive organs.*—Pistil: 1, green. Stamens: 5, fertile. Anther: White, with light blue pollen. Filament: White Resistance: Very good resistance to rain and good heat tolerance.

CHART A

| | Cas 45 | Shihi Purple |
|---|---|---|
| Flower color Black Veining | 74 A–78 A only in the middle of the flower | 74 A net-shaped veining nearly to the margin of the corolla |
| Diameter of flower | 80–85 mm | 60–65 mm |
| Growth - Habit (Length or diameter) | 90 cm | 110 cm |

It is claimed:

1. A new and distinct cultivar of petunia plant named Cas 45, as illustrated and described.

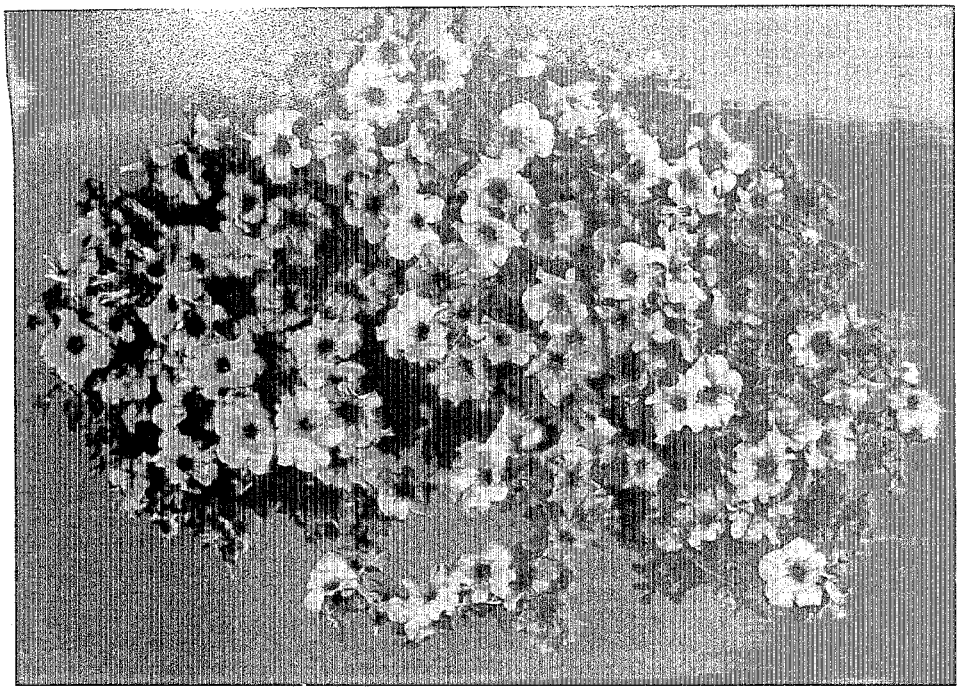

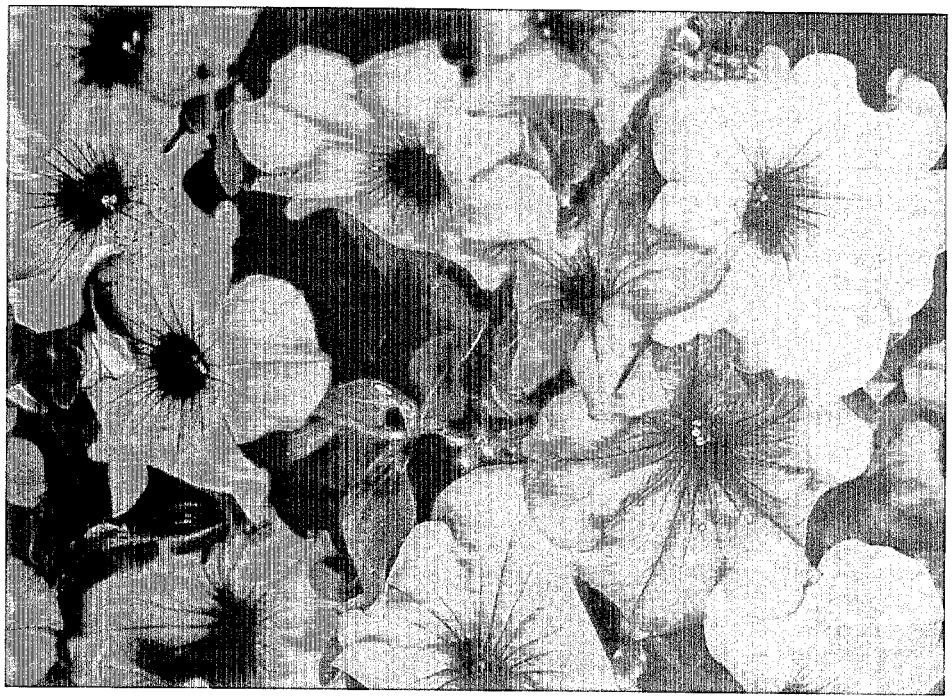

* * * * *